(12) United States Patent
Sutherland

(10) Patent No.: US 6,726,715 B2
(45) Date of Patent: Apr. 27, 2004

(54) FIBER-REINFORCED HEART VALVE PROSTHESIS

(75) Inventor: Fraser W. H. Sutherland, Boston, MA (US)

(73) Assignee: Childrens Medical Center Corporation, Boston, MA (US)

( * ) Notice: Subject to any disclaimer, the term of this patent is extended or adjusted under 35 U.S.C. 154(b) by 204 days.

(21) Appl. No.: 10/004,317

(22) Filed: Oct. 23, 2001

(65) Prior Publication Data

US 2003/0078652 A1 Apr. 24, 2003

(51) Int. Cl.$^7$ .................................................. A61F 2/24
(52) U.S. Cl. ........................ 623/2.1; 623/2.1; 623/2.12
(58) Field of Search ..................... 623/2.1, 2.12–2.19, 623/242, 900, 11.11, 66.1; 606/151; 600/37

(56) References Cited

U.S. PATENT DOCUMENTS

| | | | | |
|---|---|---|---|---|
| 4,265,694 A | * | 5/1981 | Boretos et al. | 156/242 |
| 4,731,074 A | * | 3/1988 | Rousseau et al. | 623/2.19 |
| 6,196,069 B1 | * | 3/2001 | Wiedenmeier et al. | 73/856 |
| 6,283,994 B1 | * | 9/2001 | Moe et al. | 623/2.12 |

FOREIGN PATENT DOCUMENTS

WO    WO 9832400 A1 * 7/1998 ............. A61F/2/24

* cited by examiner

Primary Examiner—David J. Isabella
Assistant Examiner—Urmi Chattopadhyay
(74) Attorney, Agent, or Firm—Robert K. Tendler

(57) ABSTRACT

A heart valve prosthesis for use as an aortic or pulmonary replacement valve, or as a mitral or tricuspid valve includes leaflets that are reinforced through the use of oriented fiber components in a laminated composite, in which the leaflets of the valve are reinforced with fiber-reinforcing materials oriented along lines of stress in the material, thus to provide a long-lived valve that provides strength at points of maximal stress that have hitherto been foci for material failure. In a preferred embodiment involving a stentless valve, the reinforcing materials are optimized in terms of the density and orientation of the fibers in the composite materials, thus to extend the life of a stentless valve, with the valve requiring no anti-coagulants as is the case with mechanical valves and exhibiting no hemolysis in which red cells are damaged by the action of mechanical valves. Longevity exceeds thirty five years in most cases, making replacement of such a valve a remote possibility. In one embodiment, oriented fiber components of various geometries are provided by laying fibers in specific orientation over a curved mold to which polymer sheets are laminated.

11 Claims, 8 Drawing Sheets

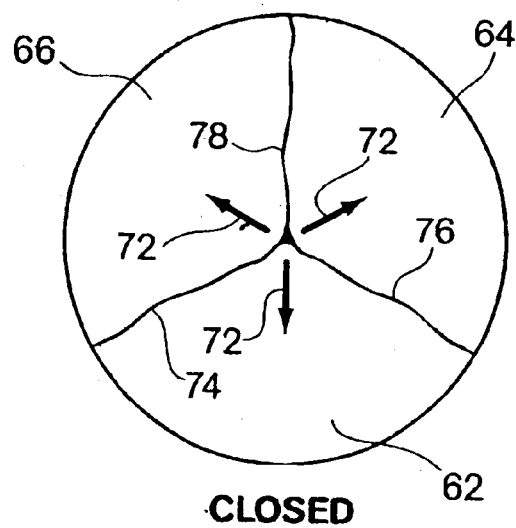
Fig. 4A CLOSED
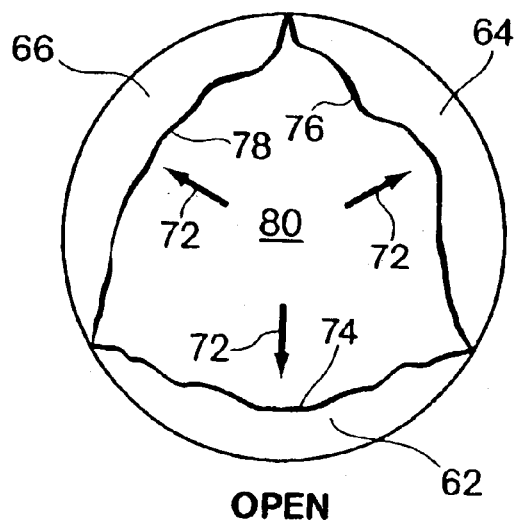
Fig. 4B OPEN

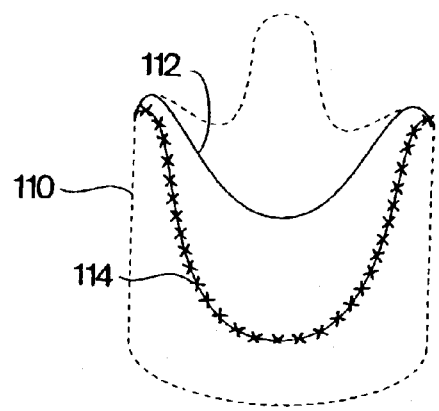
Fig. 8
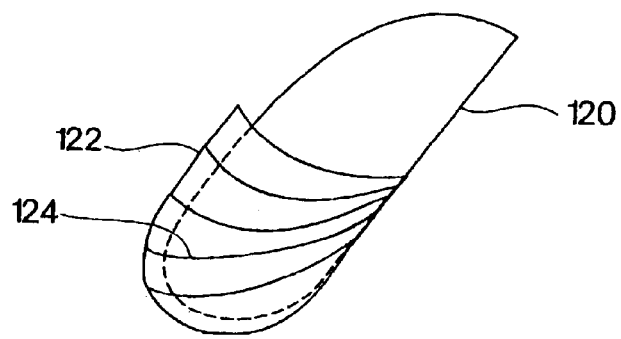
Fig. 9
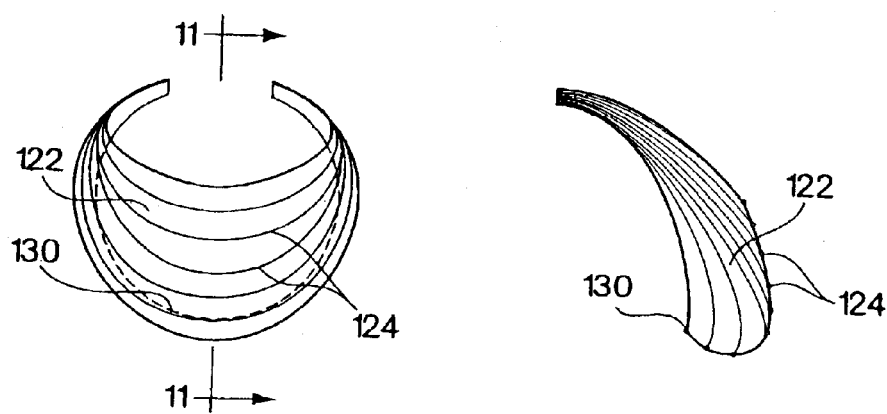
Fig. 10
Fig. 11

FIBER-REINFORCED HEART VALVE PROSTHESIS

FIELD OF THE INVENTION

This invention relates to heart valves and more specifically to a reinforced material from which heart valve leaflets can be made with reinforcing fiber strands aligned along lines of stress, thus to dramatically increase the durability and longevity of the valve.

BACKGROUND OF THE INVENTION

Artificial heart valves have been known for years and have been used to replace native valves that have become faulty through disease. The artificial heart valves themselves should ideally be designed to last for the life of the patient, in many cases in excess of thirty-five years, equivalent to over 1.8 billion heartbeats. Heart valves that can be replaced include aortic and pulmonary valves, as well as mitral and tricuspid valves.

As to the operation of normal heart valves, they open and close largely passively in response to changes in pressure in the heart chambers or great vessels i.e. aorta and pulmonary artery, which they connect. For example, the aortic valve situated between the left ventricle and the ascending aorta, opens when the rising pressure in the contracting left ventricle exceeds that in the aorta. Blood in the ventricle is then discharged into the aorta. The valve closes when the pressure in the aorta exceeds that in the ventricle.

Problems occur with the native valves when they fail to function properly through disease or trauma. Faulty valves exhibit leakage in the closed position, i.e. regurgitation, obstruction to flow in the open position, i.e. stenosis, or a combination of the two, i.e. mixed valve disease. The response of the heart to faulty valves is demonstrated by changes in the left ventricle which ensue in response to malfunction of the aortic valve. Initially the heart compensates by an increase in muscle mass i.e. hypertrophy, a process that is to some extent reversible. Eventually, however, the heart can compensate no longer and begins to dilate. This latter process is irreversible even with replacement of the faulty valve. Untreated, it leads to end stage heart failure and ultimately death. Valve replacement has become a routine operation in the developed world for patients shown to have heart valve disease who have not yet reached the stage of irreversible, end stage heart failure.

In the past, there have been two broad types of valves that have been used in replacement procedures: mechanical valves and biological valves.

Mechanical valves are constructed from rigid materials. The design of these valves takes one of three general forms: ball and cage, tilting disk or bileaflet prostheses. In general, mechanical valves have in their favor long term durability intrinsic to the very tough materials from which they are made. With a few notable exceptions, such as the well publicized Shiley CC series, mechanical failure of these valves has been very rare. Followup for some of the first generation ball and cage valves now exceeds thirty years and the longevity of more recent designs such as the latest bileaflet prostheses is expected to match these results.

The principal shortcomings of mechanical valves, however, are the need for long term anticoagulation, the tendency to cause red blood cell haemolysis in some patients and the noise created by repeated opening and closing of the valve which patients find very disturbing. Anticoagulation requires the patient to take a regular daily dose of medication that prolongs the clotting time of blood. The exact dose of medication, however, needs to be tailored to the individual patient and monitored regularly through blood tests. Apart from the inconvenience and potential for non-compliance imposed by this regimen, inadvertent over-coagulation or under-coagulation is not uncommon. Under-coagulation can lead to thrombosis of the valve itself or embolism of clotted blood into the peripheral circulation where it can cause a stroke or local ischaemia, both potentially life threatening conditions. On the other hand, over-coagulation can cause fatal spontaneous haemorrhage. It is clear therefore that anticoagulation, even in the most expert hands, is associated with finite risks of morbidity and mortality. This risk accrues significantly over the patient's lifetime. For this reason, some surgeons avoid the use of mechanical prostheses, where possible.

Hemolysis is the lysis of red blood cells in response to stresses imposed on those cells as blood crosses mechanical valves. Significant hemolysis causes anemia. These patients are required to have regular replacement blood transfusions with the attendant inconvenience, expense and risks which that entails.

Haemolysis and the need for anticoagulation result principally from microcavitation and regional zones of very high shear stress created in the flow of blood through mechanical valves. These physical phenomena are imposed on elements in the blood, i.e. red blood cells and platelets, responsible for activating the clotting cascade occasioned by the design of existing prostheses having either a rigid ball and cage, a rigid disk or two rigid leaflets.

Finally, mechanical valves may not be suitable for small patients as a significant gradient exists across these valves in the smaller sizes.

Biological valves are constructed from a variety of naturally occurring tissues taken from animals and fixed by treatment with glutaraldehyde or similar agent. Materials that have been used include dura mater from the lining of the brain, pericardium from the sac lining the heart or valve tissue itself from pigs and cows. These materials are used to fashion replacement heart valve leaflets and in the past have been assembled with the aid of a rigid supporting frame or stent. More recently leaflets made from these materials have been supported without the aid of a rigid frame and are fixed over flexible materials such as Dacron. The latter are referred to as stentless valves.

In contradistinction to mechanical valves, biological valves have flow hemodynamics that resemble the flow through native heart valves. In general, they do not therefore require lifelong anticoagulation and do not cause red cell hemolysis. Furthermore, very little residual gradient can be measured across even the smallest available stentless biological valves. Additionally, biological valves function inaudibly.

Unfortunately, however, biological valves suffer from degenerative changes over time. At least 50% of porcine valves implanted in the aortic position fail within 10–15 years post operatively. Furthermore, this risk is amplified in the mitral position and in younger patients where failure of porcine aortic valves is almost universal by five years. Progressive deterioration of biological valves manifests itself either as obstruction to forward flow through the valve in the open position, i.e. stenosis, or more commonly as tears in the valve leaflets that cause leakage in the closed position, i.e. regurgitation.

To summarize, the configuration of biological valves allows them to function inaudibly without the risks of thrombosis or hemolysis. However, the biological materials from which they are made do not have the durability to last the patient's potential lifetime.

A valve that combines the durability of man-made materials with the hemodynamics of a biological valve would be inaudible, free from the problems of anticoagulation and risk of hemolysis and yet exhibit the necessary durability to last the patient's lifetime.

This is the principal underlying development of stentless valves for the aortic or pulmonary position made from the elastomeric material, polyurethane. These valves do indeed exhibit favorable hemodynamics and have not thus far required anticoagulation. Accelerated fatigue testing has however shown that these valves do still suffer from degenerative changes in the longterm. As in the case of biological valves, degenerative changes in the materials that make up the leaflets are focused on local areas of high stress in the valve leaflets themselves and mechanical failure, not surprisingly, occurs at these exact same points. Mechanical failure is therefore a problem intrinsic to the leaflet material itself.

Polyurethane and other elastomeric polymers are isotropic when assembled as sheets i.e. they exhibit the same properties in all directions and at all points over the surface of the material. Reinforcement of elastomers with fibers improves their ability to withstand stress.

By way of further background, it will be noted that in the so-called Oxford valve, a regular uniform pattern of reinforcement is used in terms of Melinex sheets made from silicone reinforced with Terylene polyester. These were fabricated as flat sheets and then assembled as leaflets over a metal frame. The flat sheets tend to buckle in the closed position of the valve. This is because a normal valve leaflet has two axes of curvature. It is not possible to fashion a flat sheet into a surface with two axes of curvature without it buckling as is demonstrated in their valve.

In terms of the valve of Wheatley et al, European Journal of Cardio-thoracic Surgery 2000; 17:440–448, their valve is molded into curved sheets but is not reinforced. This valve showed significantly lower tendency to form blood clots than mechanical valves and improved durability over biologic valves. However, accelerated fatigue testing demonstrated calcification at wear-induced defects in the leaflet material, which were sites of subsequent material failure.

In accordance with U.S. Pat. No. 4,731,074 issued to Rousseau et al reinforced fabric is used with fibers oriented only in one direction to provide improved strength. However, this does not address the different direction and magnitude of stresses experienced in different regions of the leaflet.

The synthetic fiber reinforced stentless heart valve described by Cacciola et al, Journal of Biomechanics 2000;33:521–530, utilizes a mesh reinforcement in more than one direction. However, the patterns that they describe are regular patterns and are not specifically aligned with respect to stress lines. Such a regular matrix or mesh cannot address the regional variations in stress that exist over the entire valve leaflet due to their regularity.

SUMMARY OF THE INVENTION

In the present invention, the valve leaflets are made from composite materials and assembled in the geometric form of the native biologic valve. In the case of the aortic and pulmonary valves this is a stentless structure with valve leaflets supported respectively by the wall of the aorta or pulmonary artery only. In the case of the mitral or tricuspid valves the leaflets are supported by an annulus and additionally by chordae that extend from the free edge of the valve leaflet to the wall of the ventricle. In the case of a stented valve, for implantation into any of the foregoing anatomical positions, the leaflets are supported on a wire frame or stent to which is attached a sewing ring.

In the subject invention, mechanical properties of the leaflet material are optimized by tailoring reinforcement to those areas where it is needed, with the reinforcing strands configured in a direction and density that addresses differences in the magnitude and direction of stresses in different parts of the valve leaflet. The result of fabrication of the material over curved molds and with reinforcement of the material along lines of stress is the elongation of the lifetime of the valves by at least three times, making it unnecessary to replace the valves in the normal lifetime of an individual.

In one embodiment, the valve leaflet includes a laminated structure fabricated over a mold with two axes of curvature, with one or more layers of uninterrupted yarns, strands or fibers disposed in a continuous trajectory from one edge of the leaflet to the other edge.

The entire purpose of the reinforcing yarns, strands or fibers is to improve the fatigue resistance of the valve with fiber reinforcement in a density and direction to handle regional variations in the stresses experienced across the valve leaflet.

The principals described herein for the assembly of leaflets for replacement aortic or pulmonary valves can equally be applied to the assembly of valves for the mitral or tricuspid positions. In these latter valves the reinforcing fibers are disposed across the leaflet along lines of stress some of which continue as chordae that attach the free margin of the leaflet to the ventricular septum or free wall. Alternatively, the principals may be applied to the assembly of leaflets for use in a stented replacement heart valve.

In summary, a material for the construction of heart valve leaflets is provided through the use of oriented fiber components in a laminated composite wherein fibers are aligned along lines of stress in the material, thus to engineer fatigue resistance into the material and provide a long-lived valve that will function for the life of the patient. In a preferred embodiment, the reinforcing materials are optimized in terms of orientation of the fibers and in terms of their density. A valve constructed with flexible leaflets such as these will not require anticoagulants as is the case with mechanical valves or exhibit hemolysis in which red blood cells are damaged by the action of mechanical valves. Longevity exceeds thirty-five years in most cases, making replacement of such a valve a remote possibility. In one embodiment, oriented fiber components are provided by laying fibers in specific orientations over curved molds to which polymer sheets are laminated.

BRIEF DESCRIPTION OF THE DRAWINGS

These and other features of the subject invention will be better understood in connection with the Detailed Description and in conjunction with the Drawings, of which:

FIG. 4A is a diagrammatic illustration of the valve of FIG. 3 illustrating from a top view, the closed position of the valve, with the free margins of each of the three leaflets in apposition and with arrows indicating the direction of movement of the leaflets to open the valve;

FIG. 4B is a diagrammatic illustration of the valve of FIG. 3 illustrating the open position for the valve of FIG. 3, with the leaflets moved out from the center of the valve;

FIG. 8 is a diagrammatic illustration of a leaflet secured between two commissures along a U-shape on the interior surface of the cuff of FIG. 7, such that the free edge of the leaflet may flex as illustrated in FIGS. 4A and 4B;

FIG. 9 is a diagrammatic illustration of the formation of a valve leaflet around a heated mandrel;

FIG. 10 is a diagrammatic illustration of the formed leaflet, formed in the process illustrated in FIG. 9;

FIG. 11 is a diagrammatic illustration of the leaflet of FIG. 10, seen in profile;

DETAILED DESCRIPTION

Figure 1A:
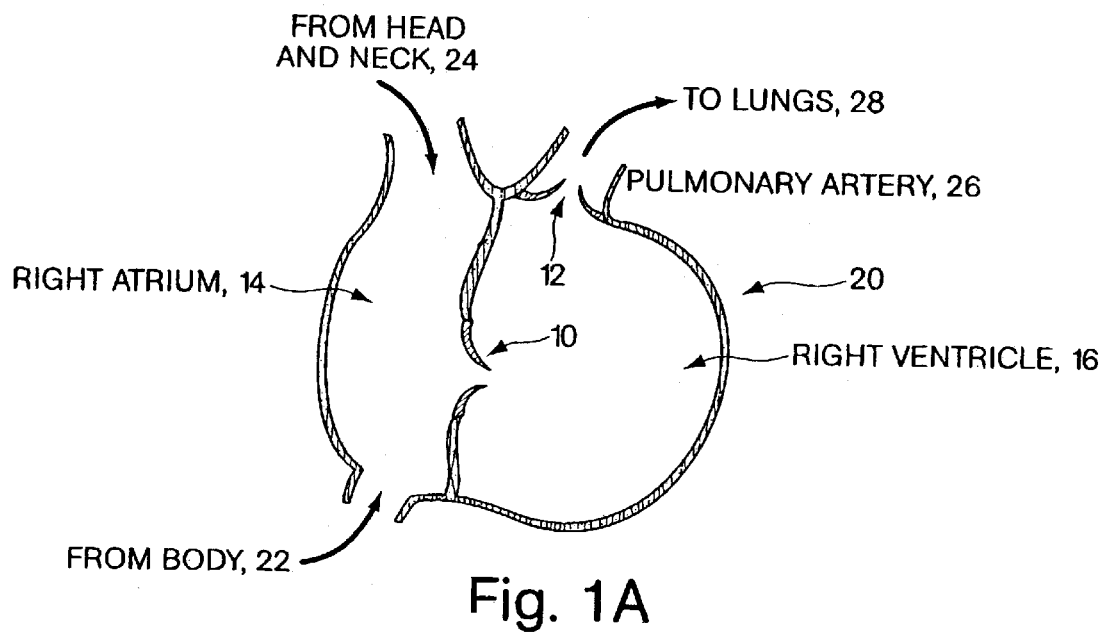
FIG. 1A is a diagrammatic illustration of the utilization of valves, both between the right atrium and the right ventricle of the heart and between the right ventricle of the heart and the pulmonary artery, showing the direction of blood flow through the heart.

Referring to FIG. 1A, a replacement valve may be positioned as illustrated at 10 and 12, in the first case between the right atrium 14 and the right ventricle 16, such that blood pumped by heart 20 from both the lower body 22, and from the head and neck 24, passes through the tricuspid valve 10 from the right atrium to the right ventricle; and from the right ventricle through pulmonary valve 12 to the pulmonary artery 26 and then to lungs 28.

Figure 1B:
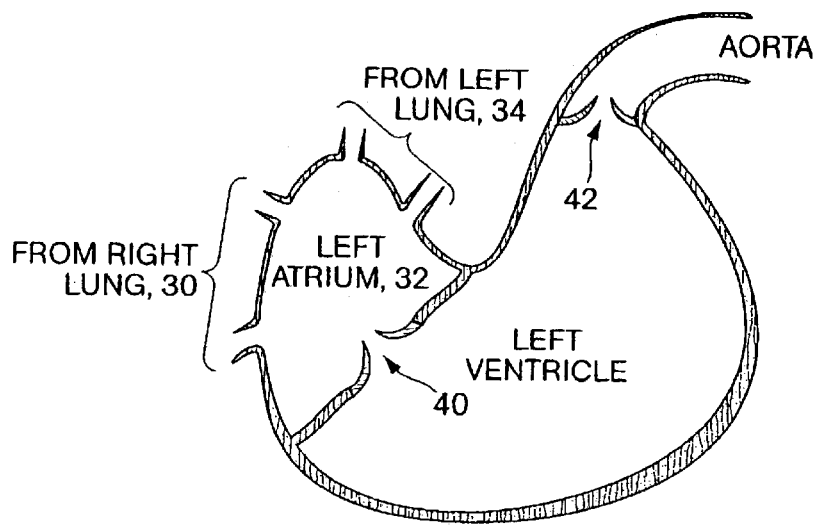
FIG. 1B is a diagrammatic representation of the placement of valves within the heart between the left atrium of the heart and the left ventricle and the left ventricle and the aorta.

With respect to the left side of the heart, and referring to FIG. 1B, blood from the right lung 30 enters the left atrium 32, and from left lung 34 to left atrium 32, where it passes through mitral valve 40 from the left atrium to the left ventricle and through aortic valve 42 from the left ventricle to the aorta. A replacement valve may be placed in either the mitral 40 or aortic 42 positions.

It will be appreciated that persons with heart conditions involving malfunctioning valves are in need of valve replacement in either of the above two scenarios. Problems occur when the valves fail to function because the valve either restricts flow in the open position, i.e. stenosis, leaks in the closed position, i.e. regurgitation or both, i.e. mixed valve disease.

Figure 2:
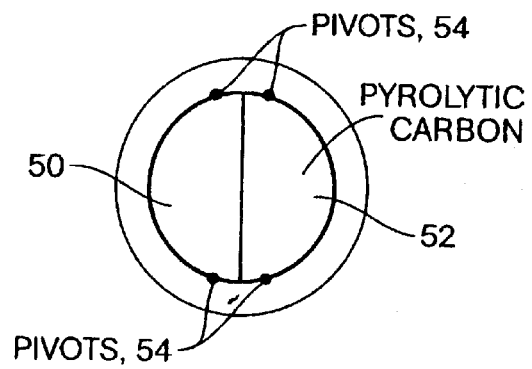
FIG. 2 is a diagrammatic representation of a mechanical valve of the bi-leaflet variety, indicating the pivoting of the two leaflets within an annular ring or collar.

As mentioned, and referring now to FIG. 2, in the past, mechanical valves have been utilized, which last somewhat longer than biologic valves and in general have moving parts that perform the valve functions. As shown in FIG. 2, a mechanical bi-leaflet valve has two leaflets, here shown at 50 and 52, which are pivoted about pivots 54 to open and close. In one embodiment of these valves, they are made of pyrolytic carbon.

While one type of mechanical valve is pictured here, it will be appreciated that there are a wide variety of mechanical valves. The main problem with the mechanical valves is the requirement for anti-coagulant drugs to be taken by the individual for his lifetime to prevent clotting on the valve, which would either cause it to malfunction or break off, i.e. embolize to other parts of the body, such as the brain, to cause a stroke. These are both life-threatening conditions.

Figure 3:
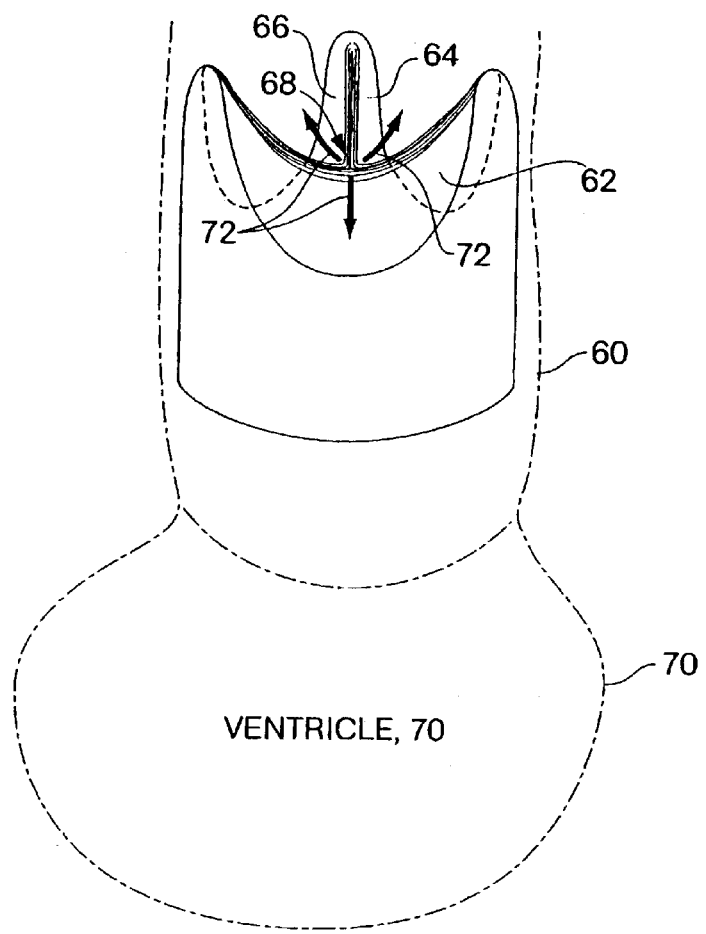
FIG. 3 is a diagrammatic illustration of the subject stentless valve involving three leaflets having free edges that come together in the closed position like a Mercedes Benz emblem, with the non-free edge attached along a U-shaped line to the wall of the aorta or pulmonary artery.

Referring to FIG. 3, what is pictured is the subject valve, in this case, an aortic valve, which is positioned in aorta 60 and includes three leaflets, here illustrated at 62, 64 and 66. These leaflets have free edges that come together as a Mercedes Benz emblem, generally illustrated at 68, in which when the valve is in its closed position, results in the edges of the three leaflets coming together and pressing against one another so as to seal blood flow from the aorta back into the ventricle, here illustrated at 70.

The valve opens through differential pressure, such that each of the leaflets has its belly moving in the direction of arrow 72, with the leaflets flexing as illustrated in FIGS. 4A and 4B. Here, as can be seen from the top view, the edges of leaflets 62, 64 and 66 are initially abutting in the sense that they have edges 74, 76 and 78 which touch each other.

As illustrated in FIG. 4B, edges 74, 76 and 78 move apart under appropriate differential pressure conditions, as illustrated by arrow 72, so as to provide a central aperture 80 through which the blood may flow.

It will be appreciated that the leaflets open and close in a period of 35 years over 1.8 billion times. It is therefore extremely important that while the valve leaflets be flexible, they not break or crack or otherwise become impaired due to the working of the valve with so many openings and closings.

Figure 5:
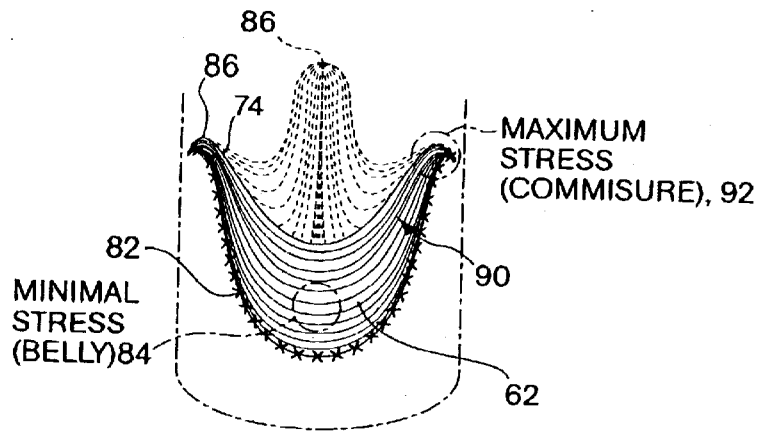
FIG. 5 is a diagrammatic illustration of one leaflet of the valve, indicating its free edge from one commissure to another, the attachment of its other, non-free edge to a cuff and the stress lines associated with the valve during usage in which the leaflet moves from the closed position to the open position, indicating maximum stress at the commissures where stress lines are close together and minimal stress in the belly of the valve where stress lines are farther apart.

Referring now to FIG. 5, it will be appreciated that leaflet 62 is shown in which an edge 82 is to be secured to a surrounding cuff, for a replacement aortic or pulmonary valve, leaving edge 74 free to flex inwardly and outwardly, as does belly 84 of the leaflet.

Leaflet 62 is slung from its cuff, to be described in connection with FIGS. 6, 7 and 8, such that not only does belly 84 move inwardly and outwardly, so does edge 74. Note that the leaflet is secured along edge 82 up to commissure 86 at the left-hand side and commissure 92 at the right-hand side, these points representing the highest points of attachment.

As can be seen by stress lines generally indicated at 90, the density and direction of the stress lines at the commissures is at a maximum, as illustrated at 92. This local stress is a point at which the leaflets have consistently been shown to fail over time.

It will be appreciated that stress is not uniformly distributed across the leaflet, and it is for this purpose that the stress in each part of a leaflet must be measured or calculated in a dynamic mode. Either through direct measurement or through calculations, it is possible to derive the stress lines associated with the material when it is assembled and functioning in the form of a heart valve leaflet.

It is the purpose of the subject invention to align the strands, fibers or yarns along these stress lines so that from a local regional point of view, the optimal amount of reinforcement is achieved. It will be appreciated that those reinforcing methods that orient fibers randomly or merely provide an arbitrary grid or mesh pattern do not take into account locally measured or calculated areas of high stress and therefore fail to address how to reinforce these regions in the most effective manner.

Having ascertained the stress lines within the leaflet, it will be appreciated one can lay out the pattern of reinforcing elements along these stress lines, thereby to alleviate stress failures at points of maximum stress, for example at the commissures.

Figure 6:
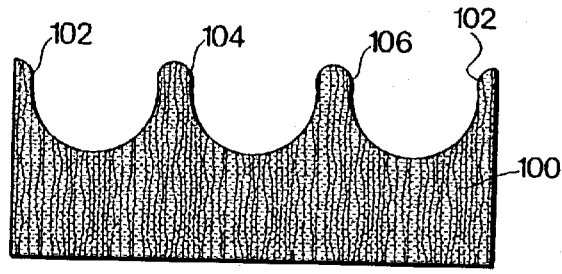
FIG. 6 is a diagrammatic view of the cuff, to which the leaflets, in one embodiment, are secured prior to its assembly.

Referring now to FIG. 6, in one method of manufacturing the subject valves, a cuff shown in an opened out position in FIG. 6 at reference character 100, has three commissures 102, 104 and 106. When the cuff is fabricated about a cylindrical or tall conical mandrel and joined, it will be seen that the resulting device is as illustrated in FIG. 7.

In general, the cuff can be made out of material such as Dacron or from the elastomer used to make the valve leaflets themselves and the cuff may be sewn into the aorta or placed otherwise so as to form the basis of the support for the leaflets in vivo. The latter is a standard operative technique for the insertion of a stentless biologic valve.

Figure 7:
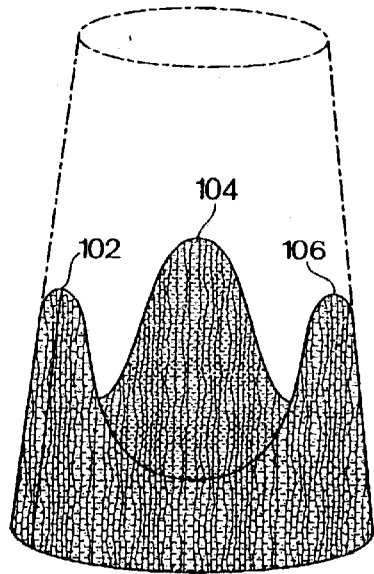
FIG. 7 is a diagrammatic illustration of the cuff of FIG. 6 in which the cuff is joined at its distal edges to form a three-dimensional object whose surface is part of a cylinder or tall cone, shown in dotted outline.

Referring now to FIG. 8, the cuff of FIG. 7 is shown in dotted outline 110, with leaflet 112 secured to cuff 110 along the edges 114, marked with an "X". The leaflets may be sewn to the cuff or otherwise affixed to the cuff such that the leaflet is supported by the cuff itself.

The leaflets themselves are laminated structures in one embodiment and have been formed via placing the laminar sheet about a heated mandrel, illustrated in FIG. 9 at 120. Here leaflet 122 is formed over the mandrel, with the reinforcing strands 124 being applied over top of the material which is to be the leaflet, and a second or more layers of material is applied.

It is important that the material of which the leaflet is formed be flexible but strong. Reinforced materials suitable for leaflet production include reinforced laminates, some of which come from the marine industry and more particularly are those that are used in the manufacture of sails. Also, fluoropolymer films, of which polytetrafluoroethylene i.e. PTFE is an example, and polyurethane, which has been used before to make heart valves, may be reinforced in accordance with the teachings of this invention.

When the leaflet is formed over the mandrel, and is heated or treated by some other physical means sufficiently to cure the resin used to secure the fibers, strands or yarns to the inside of the leaflet, then as illustrated in FIG. 10 the finished leaflet is as illustrated at 122. It will be noted that the reinforcing members run from one edge to the other of the leaflet such that strands 124, for instance, run from the edge of one commissure all the way around the belly of the leaflet to the other commissure.

FIG. 11 shows the leaflet of FIG. 10 in profile with leaflet 122 and reinforcing strands 124 in one embodiment of the subject invention, also showing a tucked back lip 130. Thus, the leaflet is formed with tucked back lip 130 which is utilized in one embodiment of the subject invention to secure the non-free edge of the leaflet to the cuff of FIGS. 6, 7 and 8.

Figure 12:
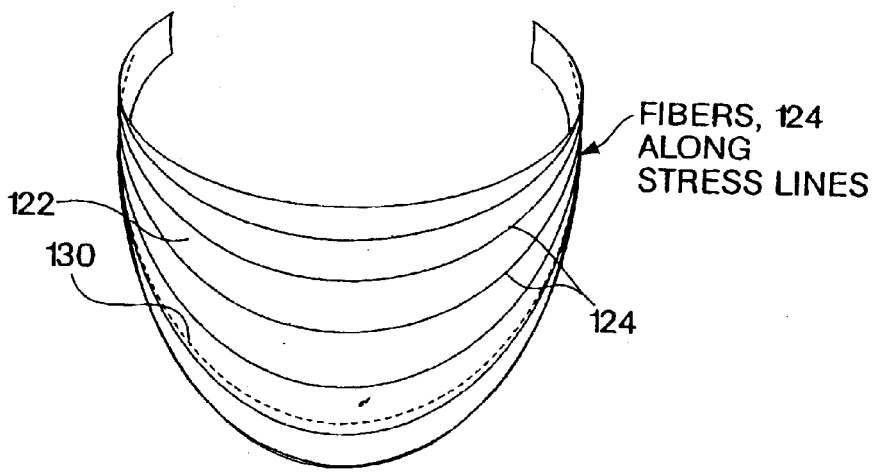
FIG. 12 is a diagrammatic illustration of the leaflet formed in the process of FIGS. 9, 10 and 11, indicating stress lines associated with the flexing of the leaflet, and along which reinforcing strands, fibers or yarns are to be placed.

As illustrated in FIG. 12, leaflet 122 has been provided with fibers 124 along the indicated stress lines such that once having ascertained where the stress lines are, appropriate reinforcement is achieved.

Figure 13:
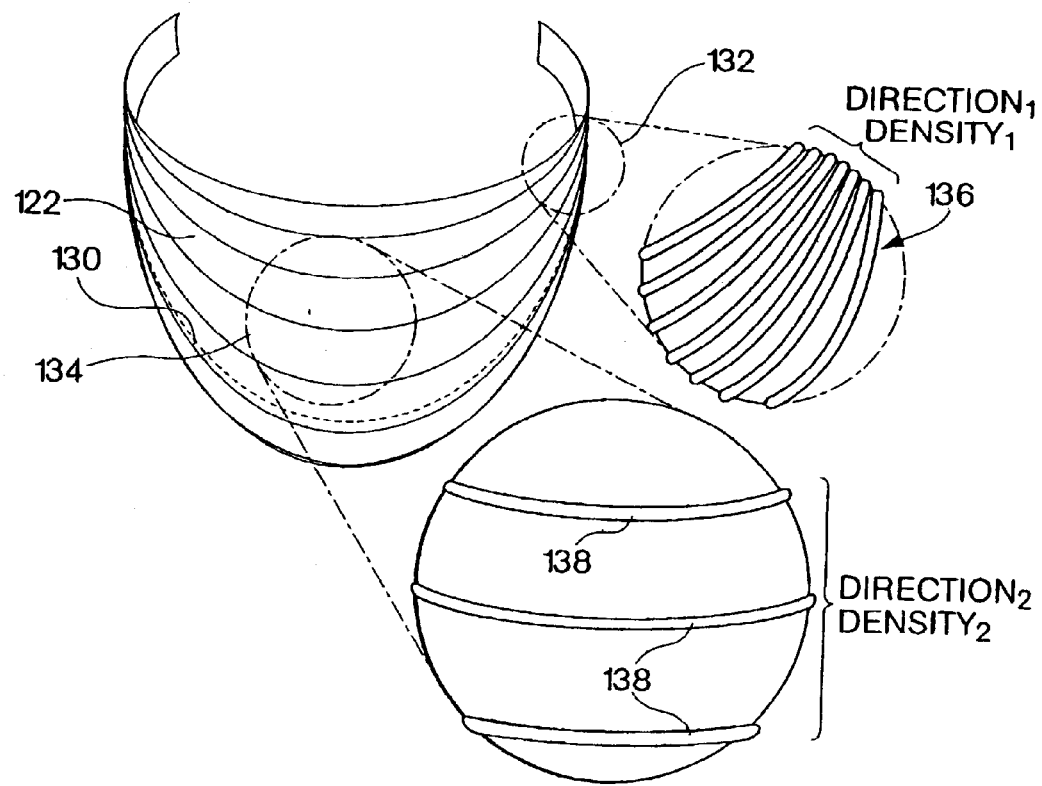
FIG. 13 is a diagrammatic representation of the orientation and density of stress lines at various regions of a leaflet of FIG. 3, noting a high density of fibers at the commissures and relatively low density of fibers in the belly of the leaflet.

Referring now to FIG. 13, it will be seen that leaflet 122 has various regions 132 and 134, which regions have differing densities and directions of stress lines. For instance, region 132 forms the apex of the leaflet at a commissure and has a high density of stress lines, as illustrated at 136. Thus the directions of the reinforcing member fibers in region 132 have a given set of directions, and a pre-determined density, whereas for region 134 in the belly of the leaflet, the stress lines 138 are a different set of directions and with different densities as illustrated.

What will be appreciated is that rather than simply providing a reinforcing mesh to reinforce leaflets, in the subject invention the reinforcement is tailored directly to the stresses that the leaflets will see during operation. The result is an increase in the number of flexings of each of the leaflets prior to failure due to the tailored reinforcing of the leaflets.

Furthermore, the construction of laminates over curved molds in this way provides a leaflet with two axes of curvature, as is the case with the native valve. The assembly of such a structure is not possible from flat sheets without buckling or overlapping.

Figure 14:
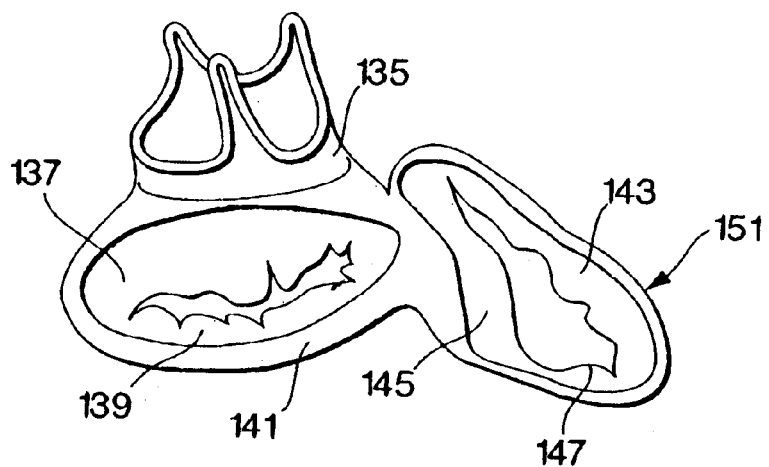
FIG. 14 is a diagrammatic illustration of the fibrous skeleton of the heart, showing the native aortic, mitral and tricuspid valves, with the view of the mitral and tricuspid valves as seen when these two valves are viewed from the left atrium and right atrium respectively, the anterior and posterior leaflets of the mitral valve being shown in the partially closed position. The pulmonary valve is hidden from view.
Figure 15:
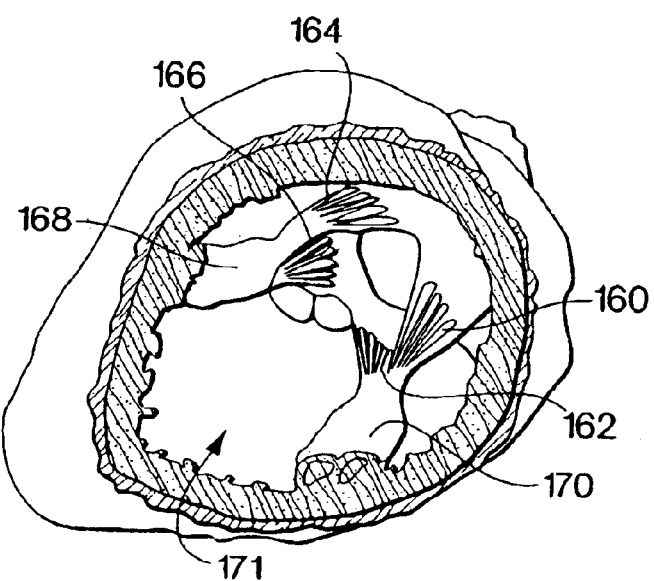
FIG. 15 is a diagrammatic illustration of the native mitral valve, viewed from inside the left ventricle to show the native mitral valve leaflets and their attachment to the anterior and posterior papillary muscles which arise from the ventricular wall.

Referring now to FIGS. 14 and 15, it will be seen that the native atrioventricular valves, i.e. mitral valve and tricuspid valves differ in structure from the native aortic valve 135 illustrated, and the pulmonary valve, not illustrated.

It will be noted that the mitral valve is situated between the left atrium and the left ventricle. It has quite different structure to that of the aortic or pulmonary valves. As will be appreciated from the fibrous skeleton of the heart, whereas the leaflets of the aortic valve are attached as though to a medieval crown, those of the mitral and tricuspid valves each attach to a ring or annulus. The mitral valve has two leaflets: an anterior leaflet and a posterior leaflet. In the closed position the line of apposition of the mitral valve leaflets appears as a smile.

In the case of the mitral valve, the non-free edge of each leaflet is attached to the margin of the annulus. The free margin is a little more complicated. In fact, little strands or chordae arise from the free margin of the valve leaflet. In the closed position of the valve, the free margin is tucked inwards so that one cannot see the chordae. The line that one sees smiling at you represents the junction of rough outer and smooth inner zones of the valve leaflet. The rough outer zone is the area of valve leaflet that is in apposition with the opposite leaflet.

As to the chordae of the mitral valve, they insert into two papillary muscles. These papillary muscles arise from the inside wall of the ventricle. In fact each papillary muscle supplies chordae to anterior and posterior leaflets. For simplicity, the chordae are considered to attach to the inside of the ventricle.

As to its operation, blood flows through the funnel-shaped orifice of the valve in response to higher pressure in the left atrium than the left ventricle. When the pressure difference reverses, the valve closes, leaflets touch over their respective rough zones and are prevented from billowing back into the left atrium by the chordal attachments to the free margin of the valve.

As with the aortic and pulmonary valves, problems arise when the valves stenose, regurgitate or exhibit a mixed pattern of disease.

As to repair, regurgitation is usually associated with floppy valve leaflets like a tired, baggy, linen sail. This can be repaired by taking tucks in the valve and by tightening the annulus with a prosthetic ring. In fact, tucks in the posterior leaflet work well, but tucks in the anterior leaflet do not. That being the case, one could replace just part of the valve, say the anterior leaflet. Some surgeons are now doing this with the same part, i.e., anterior leaflet and chordae, of a cadaveric valve or homograft. Finally, one other thing one can do if the chordae become a bit stretched, like loose sheets on a headsail, is to shorten the chordae or replace them. One can use polytetrafluorethylene (PTFE) suture material for replacement chordae or transfer chordae from one leaflet to the other. This summarizes the repair options.

As to replacement, one can excise the valve and replace it with a biologic or mechanical valve mounted on a ring. Clearly that involves sewing one ring inside another, a straightforward and widely practiced surgical procedure.

Results of valve replacement in the mitral position are, however, far inferior to those from replacement of aortic valves.

Firstly, biological valves last much less time in the mitral position, 5–8 years as opposed to 10–15 years. Thus, in general surgeons favor mechanical prostheses for the replacement of mitral valves. However, the problems described for mechanical valves in the aortic position, such as the requirement for anticoagulation, the risk of hemolysis and the noise associated with opening and closing of the valve, are also manifest by mechanical valves implanted into the mitral position.

Secondly, by dividing all of the chordal attachments to the ventricle, via papillary muscles, one removes some tethering of those parts of the ventricle to the fibrous skeleton of the heart. Those parts of the ventricle effectively have nothing to pull against. Thus replacement of the valve comes at the cost of impairing ventricular function. Sometimes one can get around this unfortunate occurrence by excising just the valve leaflets, reattaching the chordae on a rim of free leaflet margin to the annulus and sewing the prosthesis inside that. Of course, often there is not enough room in the orifice to do so.

In the subject invention, one capitalizes on the surgical difficulties as follows: A valve that mimics the normal geometry of a native valve, i.e., no need for anticoagulation, no noise, no hemolysis and the longevity of a manmade material. One then builds the leaflets with fiber reinforcement as before. This time, however, those fibers don't stop at the edge of the leaflet, they continue as the chordae and get attached to the papillary muscles. Note, these fibers are truly load bearing. Two such leaflets are mounted on an annulus that one can sew inside the native annulus, with the chordae of the valve then sewn to the papillary muscles.

Note that one can provide tethering of the ventricle with the prosthetic chordae of the subject valve and thereby retain left ventricular function and all the advantages that are described above.

Note, St. Jude is testing a similar biologic valve, the so-called Quatro valve, so called because it has four leaflets. However, this is a biological valve and there is none of the subject reinforcing.

The anterior mitral valve leaflet could be used as a part valve replacement or form part of the entire mitral valve replacement. The leaflet has the non-free margin attached along a line to a ring or annulus. Fibers are disposed through the body of the leaflet along stress lines and extend as chordae from its free margin. Chordae or strands which insert into a fixing device may, for example, be of the same material as the leaflet itself. A variety of techniques of attachment are possible to the wall of the ventricle, either as a patch on the inside or through the wall of the ventricle onto a pledget on its outer surface.

The posterior leaflet has a slightly different geometry than that of the anterior leaflet, although it is fabricated in the same manner as above. In this instance, the non-free margin is also attached to the annulus. Once again, fibers are disposed across the leaflets, which end up as chordae.

The anterior and posterior valve leaflets are assembled in one embodiment by attachment of their non-free margins to a common annulus. Chordae from the right-hand side of the valve from both leaflets will be attached to the ventricle by a common attachment. Similarly, chordae from both anterior and posterior leaflets on the left-hand side of the valve will be attached by a common attachment, more specifically.

More particularly, referring now to FIG. 14, in which the mitral and tricuspid valves are seen as they would be from the left atrium 32 of FIG. 1B and right atrium 14 of FIG. 1A respectively, it will be appreciated that the mitral valve has two leaflets, an anterior leaflet 137 and a posterior leaflet 139. The anterior and posterior leaflets of the mitral valve are supported by a fibrous ring or annulus 141. The tricuspid valve has three leaflets, an anterior leaflet 143, a septal leaflet 145 and a posterior leaflet 147. These are also supported at their periphery by an annulus 151.

Referring now to FIG. 15, which shows the mitral valve seen from the opposite side i.e. from inside the left ventricle, strands or chordae 160, 162, 164, 166 arise from the free edge of the native mitral valve leaflets and attach to the inside of the left ventricle at the anterior papillary muscle 168 and posterior papillary muscle 170. The papillary muscles are seen to arise from the wall of left ventricle 171. Chordae from one side of the anterior leaflet 162 unite with chordae from the same side of the adjacent poterior leaflet 162 to form a common attachment with the posterior papillary muscle 170. The arrangement is essentially symmetrical on the other side with chordae 164 and 166 from the anterior and posterior leaflets respectively uniting to attach to the anterior papillary muscle 168.

Figure 16:
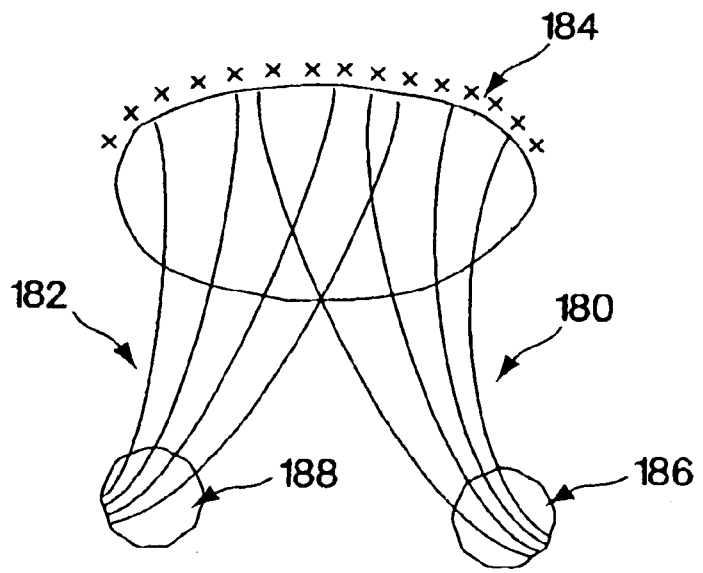
FIG. 16 is a diagrammatic illustration of a leaflet fabricated for the assembly of a replacement mitral or tricuspid valve; and, FIG. 17 is a diagrammatic illustration of a wire stent and the attached wire annulus used in the assembly of a stented valve.

FIG. 16 illustrates another embodiment, which may be used to assemble replacement mitral or tricuspid valves in whole or part. Fibers embedded in or secured to the leaflet, and oriented along stress lines, continue from the free edge as strands or chordae and are divided into two groups 180 and 182. Two or more of these leaflets with their attendant chordae may be sewn or attached by another suitable manner along a line marked by crosses at their periphery 184 to a ring or annulus. This annulus will be sewn inside the ring of fibrous tissue that surrounds the mitral valve orifice after excision of the diseased valve. Fibers from adjacent sides of the two leaflets are brought together distally and are embedded or secured to a second sheet or sheets of polymer, 186 and 188 each of which will be sewn to either the anterior or posterior papillary muscles, sewn through the wall of the ventricle at a suitable point or attached in other suitable manner to the ventricular wall. The surgical techniques described here for implantation of the subject replacement heart valve are standard techniques for the insertion of cadaveric mitral valves or parts thereof with their subvalvar apparatus into the mitral or tricsupid positions. A similar surgical technique is known and employed for the insertion into the mitral position of the Quattro® biologic valve, made by St Jude Medical.

Figure 17:
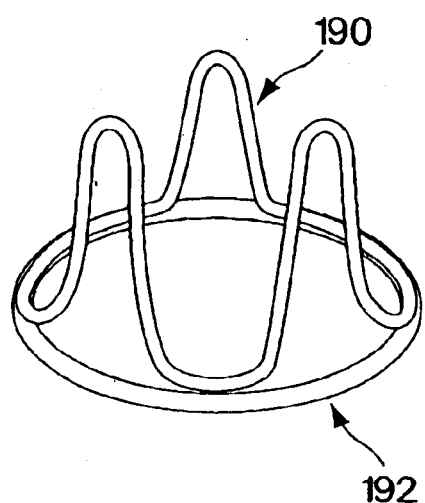

Referring now to FIG. 17, in a third embodiment, fiber reinforced leaflets may be assembled over a wire stent that takes the form of a crown 190 and is itself mounted on a ring 192. The latter ring may be covered in a material, such as Dacron, that holds surgical sutures. This is a known method used for the assembly of stented biological valves which are then implanted into the aortic, pulmonary, mitral or tricuspid position by sewing the valve ring to the orifice that remains after excision of diseased valves from each of these anatomical sites using standard surgical techniques practiced by heart surgeons throughout the world.

Note that in all of the above-mentioned valves, the leaflets are reinforced by fiber, strands or the like, along predetermined stress lines.

What now follows is a more detailed description of the manufacture of the leaflets.

MANUFACTURING PROCESS

It will be appreciated that each of the leaflets is to be made of a flexible material approximating a kind of a diaphragm. In general, the leaflet is made of an elastomeric polymer in which is embedded fibers, strands or other structural members that, in the preferred embodiment, they have a density and direction corresponding to the stress lines at various points or regions within the leaflet.

In order to manufacture such a leaflet, the leaflet may be made from one or more sheets of plastic materials such as Teflon®, polyurethane, Mylar® or other type of laminatable material and is positioned over a heated mandrel. The material is provided with a resin and the fibers, strands or other strengthening members are laid over the sheet and bound to it by the resin, with various sheets of material either underlying the strands or overlying the strands, or both, such that the leaflet is built up in a laminated fashion in one embodiment. Thus the leaflet may be composed of one or more layers, with the fiber, strands or structural members either embedded therein or secured thereto.

The leaflet when formed over the mandrel is heated so as to bond the fibers to the underlying sheet, whereupon the structure is cooled. It will be appreciated that the fibers can also be bonded using a variety of other physical techniques such as, but not limited to, electron beam curing or the use of microwave radiation.

In one embodiment, each of the leaflets is then attached to a support cuff, which preferably is made of Dacron, or the same material as the leaflets, with the free edges of the leaflet exposed in the center of the cuff and with the non-free edges to be attached to the cuff in an appropriate manner. As will be appreciated, the non-free edges of the leaflet may be affixed to the cuff in any convenient manner such as by bonding.

In one embodiment, three leaflets are utilized, with the non-free edges of each of the leaflets affixed to the appropriate surfaces or edges of the cuff. The cuff edges to which the non-free edges of the leaflets are sewn or affixed are U-shaped in nature, juxtaposed at a point called the commisure, with leaflets positioned such that their free edges, in the closed position of the valve, resemble a Mercedes Benz emblem, with the free edges of each of the adjacent leaflets touching each other in the closed position of the valve, such that blood is prevented from going from one side of the valve to the other.

When the valve is to be opened, pressure forces the free edges of the leaflet apart so as to provide an aperture through the cuff, through which the blood flows.

In another embodiment, for assembly of a mitral or tricuspid valve, fibers embedded in or secured to the valve leaflet and constructed in the manner described above are led away from the free margin and are embedded in or secured to a second sheet or sheets of film. Two leaflets are required to construct a replacement mitral valve. The anterior leaflet and posterior leaflet are, however, assembled separately, taking into account the individual size and shape of each and the specific density and orientation of fibers along stress lines in each. The non-free edge of each leaflet is then attached to part of the circumference of an annulus or ring. The latter is made from steel wire or other suitable material.

In a third embodiment, valve leaflets are wrapped over a wire stent or frame to which is attached a sewing ring. Once again, the orientation and density of fibers required in these leaflets is tailored to the specific stress lines that are imposed on the leaflets by this mode of assembly.

In each of the embodiments described, the result of such a construction is that those portions of each leaflet which are stressed to a greater degree and which have traditionally been points of failure are provided with more reinforcement along the stress lines, with reinforcement being tailored to the types of stress at that particular area of the leaflet.

The result is that the longevity of the resulting valve, stentless or otherwise, is increased due to the reinforcing along predetermined stress lines, which stress lines can be ascertained through any variety of techniques used to examine the leaflet structure in a dynamic mode. The techniques can be photographic, holographic or mathematical models that determine the local stress densities.

Having ascertained the local stress densities, the appropriate reinforcing along the local stress lines is provided during the manufacturing process. Note that the longevity of such valves is at least three times that of the biologic valves to which they have been previously compared.

As to the reinforcing fibers themselves, they include carbon fibers, polyester fibers such as Vectran® which is made by Hoescht Celanese, fibers made from the aramids Kevlar® which is made by DuPont, Twaron® which is made by the German company Akzo and Technora® which is made by the Japanese company Teijin, and also polyethylene fibers such as Dynema, which is manufactured by DSM of Holland, Certran® which is manufactured by Hoescht Celanese or Spectra® which is made by the Allied-Signal Corporation.

If carbon fibers are utilized they must be somewhat flexible. They are in essence high in tensile strength but however, are configured to have a diameter that elongates by at least 2% before breaking. As a result, carbon fibers should be preferably in the 2–3,000ths of an inch in diameter.

It will be noted that fiber-reinforcing materials for sails would result in a leaflet that is too stiff. This is because the reinforcing carbon fibers are those in the 7–10,000ths diameter range.

In general, while carbon fiber has been utilized for reinforcing of sails, it may be desirable to take advantage of the elasticity of polyester strengthening agents so as to improve the flexibility of the leaflets during operation. While sails need to hold their shape and are to be rigid under various wind-loading conditions and thus require relatively rigid strengthening members, in heart valves, the leaflets need to be able to flex in a dynamic sense as opposed to the static sense in which sails are used during, for instance, yacht racing.

It will also be appreciated that the sheet or film from which the leaflet is preferably formed is Teflon® or polyvinyl fluoride. In the usual embodiment, the fibers are sandwiched between two such sheets and films, although technically it is possible to adhere the reinforcing strands, fibers or members to one side of the sheet through the aforementioned resins.

It will be appreciated that the resin surrounds the fibers and at room temperature is tacky. When cured with temperature and pressure or other physical technique the resin serves to bind the fibers or reinforcing filaments to a sheet or a film that forms the leaflet. In one embodiment, the resins are thermoset.

The time temperature profiles or other physical conditions required for a particular resin depend on the underlying fibers and sheets utilized, with resins and materials utilized in sails for sailing vessels being useable in the subject application.

TABLE I

| Leaflet material | Teflon |
| --- | --- |
| Reinforcing material | Dynema |
| Reinforcing material diameter | 150 microns |
| Reinforcing material Young's Modulus | 20,000,000 |
| Resin | silicon rubber |
| Number of layers | 2 |
| Curing temperature | 250 degrees F. |
| Curing time | 1–2 hours |

Having now described a few embodiments of the invention, and some modifications and variations thereto, it should be apparent to those skilled in the art that the foregoing is merely illustrative and not limiting, having been presented by the way of example only. The principal of tailoring the alignment of fibers to anticipated regional stress profiles in heart valves may equally be applied to the fabrication of textiles with open pore structures to be used as scaffolds for the tissue engineering of heart valves. Indeed, numerous modifications and other embodiments are within the scope of one of ordinary skill in the art and are contemplated as falling within the scope of the invention as limited only by the appended claims and equivalents thereto.

What is claimed is:

1. A leaflet for a heart valve having an improved lifetime, comprising:

a sheet of flexible material configured in the form of said leaflet; and, a number of stress-relieving highly flexible fine fibrous elements affixed to said sheet and having lengths which are aligned with predetermined stress lines corresponding to lines of stress in said leaflet when said leaflet is deployed in said valve and said valve is operated so as to flex said leaflet.

2. The leaflet of claim 1, wherein the stress relieving elements run from one edge of said leaflet to another.

3. The leaflet of claim 2, and further including a cuff having opposing commisures, wherein opposed portions of said leaf are attached to opposed commisures, and wherein said stress relieving elements run from the portion of one leaflet attached to one commisure to the portion of said leaflet attached to said opposing commisure.

4. The leaflet of claim 3, wherein the density and direction of the stress lines in said leaflet at the point of attachment to a commisure differs in direction and density at other areas of said leaflet such that the direction and density of said stress relieving elements is tailored to the stresses to be experienced by said leaflet in the operation of said valve.

5. In a heart valve, a heart valve leaflet having stress relieving highly flexible fine fibrous elements tailored in density and direction to expected stresses within said leaflet when said heart valve is in operation.

6. The heart valve leaflet of claim 5, wherein said heart valve is an aortic valve.

7. The heart valve leaflet of claim 5, wherein said heart valve is a pulmonary valve.

8. The heart valve leaflet of claim 5, wherein said heart valve is a mitral valve.

9. The heart valve leaflet of claim 5, wherein said heart valve is a tricuspid valve.

10. The heart valve of claim 5, wherein said stress relieving fibrous elements are selected from the group consisting of fibers, strands and filaments.

11. The heart valve of claim 10, wherein said leaflet includes a flexible sheet and wherein said stress relieving fibrous elements are affixed to said sheet in predetermined directions and densities corresponding to the direction and density of local stress lines within said leaflet corresponding to said expected stresses.

* * * * *